United States Patent [19]

Hanson et al.

[11] 4,261,339

[45] Apr. 14, 1981

[54] BALLOON CATHETER WITH ROTATABLE SUPPORT

[75] Inventors: Bruce L. Hanson, Wayne, N.J.; Sidney Wolvek, Brooklyn, N.Y.

[73] Assignee: Datascope Corp., Paramus, N.J.

[21] Appl. No.: 883,513

[22] Filed: Mar. 6, 1978

[51] Int. Cl.³ .................................... A61M 29/02
[52] U.S. Cl. .................................. 128/1 D; 128/344; 128/348
[58] Field of Search ............... 128/1 D, 246, 325, 344, 128/348-351

[56] References Cited

U.S. PATENT DOCUMENTS

| | | | |
|---|---|---|---|
| 3,504,662 | 4/1970 | Jones | 128/344 |
| 3,692,018 | 9/1972 | Goetz et al. | 128/344 |
| 3,837,347 | 9/1974 | Tower | 128/344 |
| 3,877,838 | 4/1975 | Choy | 128/344 |
| 3,900,033 | 8/1975 | Leininger et al. | 128/344 |
| 3,939,820 | 2/1976 | Grayzel | 128/344 |
| 3,978,863 | 9/1976 | Fettel et al. | 128/349 B |

FOREIGN PATENT DOCUMENTS

| | | | |
|---|---|---|---|
| 2456980 | 6/1976 | Fed. Rep. of Germany | 128/349 R |
| 955490 | 4/1964 | United Kingdom | 128/349 R |

Primary Examiner—Robert W. Michell
Assistant Examiner—C. F. Rosenbaum
Attorney, Agent, or Firm—Kenyon & Kenyon

[57] ABSTRACT

An inflatable and deflatable balloon catheter is disclosed. The inflatable chamber of the catheter is supported about an elongated support member of small diameter. One end of the support member is rotatable relative to the chamber wherein the chamber is adapted to being compactly twisted about the support member upon swiveling or rotation of the support member. The compactly twisted chamber has a small diameter whereby insertion of the catheter through a small incision and guiding thereof in a small body canal or passage is facilitated. A smooth-walled sheath of low friction material is disclosed for enclosing the twisted chamber to facilitate atraumatic entry of the catheter into the incision or body opening and for facilitating insertion and movement of the catheter. The support member is preferably made of a material which may be formed during use into a desired axial configuration by bending. Balloon catheters according to the present invention are advantageously used for intra-aortic balloon pumping.

36 Claims, 7 Drawing Figures

BALLOON CATHETER WITH ROTATABLE SUPPORT

BACKGROUND OF THE INVENTION

1. Field of the Invention

The present invention relates to catheters and more particularly to an inflatable balloon catheter, particularly for use in intra-aortic pumping.

2. Description of the Prior Art

Intra-aortic balloon pumping is a recognized method of cardiac assistance for a failing heart. It is also a recognized method of treating cardiogenic shock and has been used to help wean a patient away from cardiopulmonary bypass, to support a patient during a difficult postoperative period, and to provide a pulsatile flow to the linear flow supplied by the cardiopulmonary bypass device. Intra-aortic balloon pumping has also been used therapeutically after myocardial infarction to limit the extension of necrosis and has been used as a therapy for angina pectoris.

Catheters for intra-aortic balloon pumping presently utilize a nonstressed or nondistensible balloon, i.e., the balloon is not stretched during inflation and deflation and substantially never changes its surface area, inflating and deflating with a predetermined volume of appropriate fluid to achieve phasic operation; the balloon surface area is always substantially equal to that of a fully inflated balloon. The intra-aortic balloon catheters of the prior art are relatively stiff and bulky and have a large "entering" cross-section. The femoral artery has heretofore been used for insertion of these stiff and bulky intra-aortic balloon catheters because of the large diameter of that artery. However, considerable surgery must be performed in order to reach and isolate the femoral artery. In addition, a large incision must be made in the femoral artery wall to permit introduction of these prior art devices. The safeness of intra-aortic balloon pumping using the catheters of the prior art has been questioned since they can cause and in some instances have caused aortic dissections, perforations and trauma mainly because of the entering size and the relative stiffness of the devices. Additionally, this stiffness prevents precise maneuverability of the catheter within the vascular structure and thereby limits its potential for efficacy.

It is recognized in the prior art that insertion and guiding of catheters is difficult and that trauma and damage to the incision and blood vessel may occur during said insertion and guiding. The balloon of prior art catheters is commonly rolled or spirally wrapped around its underlying catheter tube in order to insert it into and guide it in a blood vessel. In Grayzel, U.S. Pat. No. 3,939,820, an attempt is made to obtain a tight wrap in which the size of the enclosed catheter tube is decreased by replacing it with a thin support member or wire. The balloon membrane, however, must still be wrapped, or rolled, and the limited amount of balloon material available and the limited magnitude of the torsional stres that may be applied to twist the balloon limit the tightness of the roll regardless of whether the balloon is twisted around a catheter tube or around a thin support member. In catheters of the prior art, the balloon tip and gas supply tube are rigidly connected to each other within the balloon (Goetz et al., U.S. Pat. No. 3,692,018 and Jones, U.S. Pat. No. 3,504,662), or are rigidly connected to each other by a thin support member within the balloon (Grayzel, U.S. Pat. No. 3,939,820), or are connected to each other within the balloon by a non-twistable, copper current-carrying braid (Kantrowitz et al., U.S. Pat. No. 3,585,983). The twisting of the balloon about its longitudinal axis is therefore limited since no rotational displacement is possible between the balloon tip rigidly fastened to the distal end of the balloon and the catheter tube or support means rigidly fastened to the proximal end of the balloon.

SUMMARY OF THE INVENTION

In accordance with the present invention, a new and improved catheter is provided in which the chamber or inflatable balloon of the catheter may be tightly twisted into a small cross-sectional diameter. A smaller entering diameter for the catheter may thereby be obtained enabling the catheter to be inserted into smaller incisions and body openings and guided through smaller and more tortuous canals and passageways.

It is an object of the present invention to provide a new and improved catheter.

It is also an object of the present invention to provide a catheter capable of being configured into a cross section no larger than that of the inflating gas supply tube of the catheter.

It is an object of the present invention to provide a catheter which may be inserted through small incisions or even by percutaneous insertion.

It is another object of the present invention to provide a catheter having a chamber and support means therefor which are relatively rotatable.

It is still another object of the present invention to provide a catheter incorporating a sheath facilitating atraumatic insertion of the catheter into blood vessels or body openings.

It is yet another object of the present invention to provide a catheter capable of being axially shaped or formed by the surgeon to facilitate passage of the catheter into a tortuous blood vessel or bifurcation.

It is another object of the present invention to provide single and multi-chambered catheters embodying the aforementioned objects.

In accordance with the invention, the chamber of the catheter is supported about support means, one end of the support means being rotatable relative to the chamber wherein the chamber is adapted to being compactly wrapped, rolled or twisted about the support means upon rotation of the chamber which causes swiveling of the support means. The support means is of small diameter and is disposed within the chamber connected with the chamber at one end thereof and rotatable with respect to the remainder of the catheter at the other end of the chamber whereby the support means may be rotated or swiveled relative to the catheter. Rotatable disposition of the support means in the catheter chamber at one end thereof permits tight twisting of the chamber about the support means without distorting or damaging the conduit means for transmitting fluid into and out of the chamber. Thus, the torque applied to the chamber in twisting it is not imparted to the conduit means and the remainder of the catheter.

In the preferred embodiments, the chamber and support means are connected at the distal end of the chamber, and the support means are rotatably disposed in the conduit means or catheter tube at the proximal end of the chamber, distal and proximal being referenced with respect to the connection of the chamber to the conduit means. Also in the preferred embodiments, the catheter is utilized for intra-aortic balloon pumping.

A catheter according to the disclosed embodiments of the invention comprises gas supply means for transmitting gas into and out of the balloon and an elongated, rod-like support member in the balloon for supporting the balloon, the proximal end of the balloon being non-rotatably connected to the gas supply means and the support member being rotatably secured to the gas supply means. Means are provided to prevent the rotatable support member from telescoping or collapsing as the catheter is inserted and guided during use. The distal end of the balloon is non-rotatably connected to the support member. The balloon is wrapped about the support member by rotation of the distal end of the balloon.

In accordance with another aspect of the invention, a sheath is provided to enclose the balloon in the wrapped configuration thereof. The sheath is thin-walled, smooth and has a low coefficient of friction to thereby facilitate entry and guiding of the catheter and to reduce trauma.

In accordance with still another aspect of the invention, the support means is a thin flexible wire which may be formed into and retain a desired axial shape during use. This enables the catheter to be guided into and through a bifurcation or tortuous body canal or vessel.

Smaller entering diameters and controllability of catheters according to the invention, combined with the ease of insertion, makes it possible to insert such catheters into smaller and more accessible arteries than the femoral artery, for example, the brachial or the auxillary artery. Intra-aortic balloon pumping can be carried out with catheters according to the invention without undergoing the extensive surgery of a femoral arteriotomy and therefore may become available to mamy more patients. Those patients for whom the standard transfemoral approach is impossible because of atheromatous femoral arteries, obstructive aortoiliac disease, or a contaminated or previously cannulated groin may now be treated by the more easily inserted and more flexible catheters of the invention.

It is therefore contemplated that the catheters according to the present invention will make intra-aortic balloon pumping available to many more people than can now be treated by the use of the relatively stiff, bulky prior art balloon catheters and the obligatory use of the femoral arteries because of the large "entering" bulk of the prior art catheters.

It is also within the contemplation of the present invention that the catheters of the invention be percutaneously insertable, i.e., insertable through the skin without surgery.

These and other aspects of the invention will be more apparent from the following description of the preferred embodiments thereof when considered with the accompanying drawings and appended claims.

BRIEF DESCRIPTION OF THE DRAWINGS

The present invention is illustrated by way of example and not limitation in the figures of the accompanying drawings in which like references indicate similar parts and in which.

DESCRIPTION OF THE PREFERRED EMBODIMENTS

Figure 1:
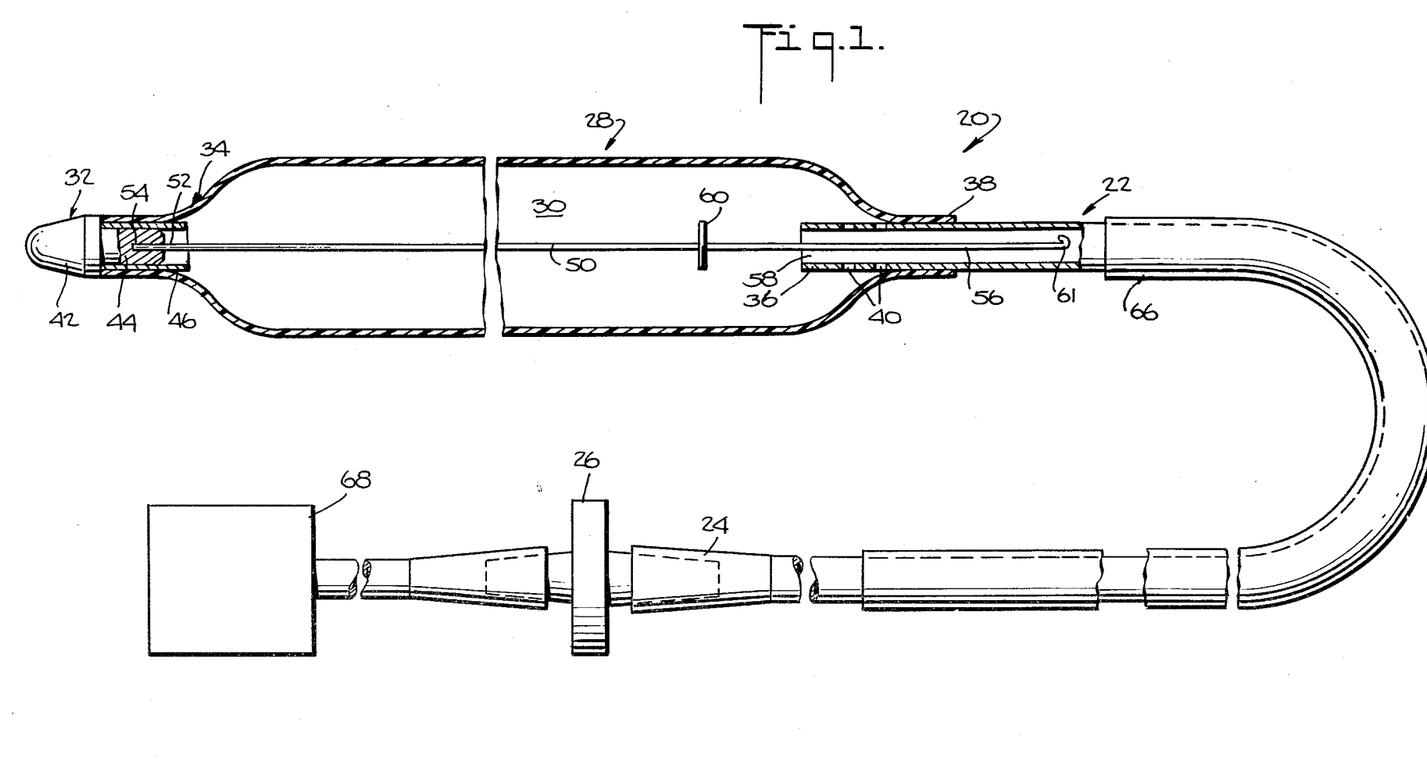
FIG. 1 is a side view, partly in section, of the catheter according to the invention showing the balloon thereof in an untwisted configuration.

As shown in FIG. 1, catheter 20 according to the invention includes a hollow, flexible catheter gas supply tube 22 affixed at one end 24 thereof to connector 26 and adjacent the other end thereof to an elastomeric balloon 28. Catheter 20 is an omnidirectional intra-aortic balloon catheter and includes the single balloon chamber 30. In accordance with the preferred embodiments illustrating the invention and not by way of limitation, the balloon is not stressed during inflation and deflation, i.e., the balloon is non-distensible and has substantially the same surface area when inflated and when deflated. A rigid tip 32 is fluid-tightly affixed to the distal end 34 of the balloon. The gas supply tube 22 terminates in end 36 adjacent proximal end 38 of balloon 28 which is disposed within chamber 30 of balloon 28 a small distance sufficient to accommodate within chamber 30 a plurality of gas ports 40 in gas supply tube 22. The gas ports 40 communicate the interior of the gas supply tube with chamber 30. The proximal end 38 of the balloon is fluid-tightly bonded circumferentially to gas supply tube 22 and the distal end 34 of the balloon is fluid-tightly bonded circumferentially to tip 32 by, for example, an adhesive or by welding. The tip, balloon and gas supply tube are coextensive at least in part to form a continuous member having good flexibility at the junction of the tip and balloon and the gas supply tube and balloon.

Tip 32 includes an end portion 42 having a section 44 of reduced diameter and a sleeve 46. The sleeve is fluid-tightly circumferentially bonded about section 44 and the balloon end is fluid-tightly circumferentially bonded to the sleeve by, for example, an adhesive or by welding. The parts of tips 32, sleeve 46 and tube 22 within chamber 30 are smoothly contoured to reduce stress and wear on the balloon during operation thereby preventing puncturing, cutting or rupturing of the balloon.

Interposed between tip 32 and tube 22 in chamber 30 is support wire 50. End 52 of the support wire is non-rotatably secured in hole 54 of tip 32 and end 56 is rotatably disposed in opening 58 of tube end 36. End 52 extends into tip 32 and is soldered therein or non-rotatably affixed therein by other means such as adhesives, for example. End 52 abuts against the end of hole 54 and together with the non-rotatable affixing of end 52 to tip 32 prevents movement of wire 50 towards the distal end 34 of the balloon. A disc-shaped keeper 60 secured to the wire 50 adjacent tube end 36 prevents movement of the wire toward the proximal end 38 of the balloon and prevents the wire from being forced further into the end of tube 22 when pressure is applied to the balloon during insertion of the catheter. Opening 58 permits wire 50 to rotate freely therein. The end 56 of the wire extends sufficiently into tube 22 to prevent the wire from being withdrawn through opening 58. Wire end 56 at the extremity 61 thereof is rounded to prevent damage to the wall of tube 22.

In accordance with the invention, the provision of the thin support wire 50 rotatably disposed in the gas supply tube permits the support wire to be rotated or swiveled relative to the gas supply tube, thereby permitting the balloon to be easily and compactly twisted about the support wire. This results in the twisted balloon having a smaller cross-sectional area which approaches that of tip 32 and gas supply tube 22. Thus, the overall cross-sectional area of catheter 20 may be reduced for insertion into smaller incisions. Additionally, the torque applied to twist the balloon during wrapping thereof is not imparted to the gas supply tube thereby preventing stress to and damage of the gas supply tube.

Figure 2:
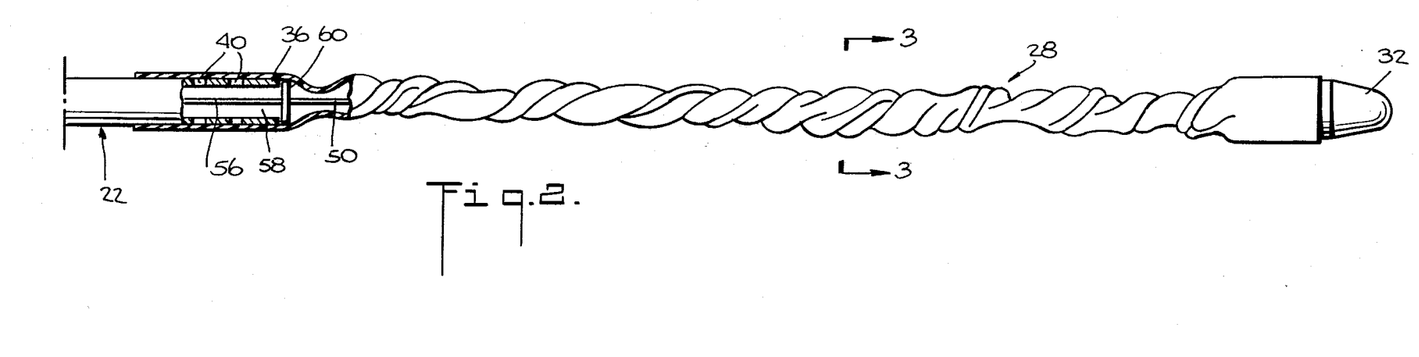
FIG. 2 is a side view, partly in section, showing the balloon of the catheter of FIG. 1 in its twisted or wrapped configuration.
Figure 3:
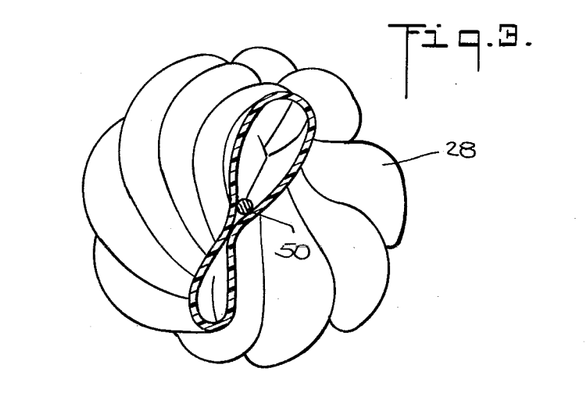
FIG. 3 is a section view taken along 3—3 of FIG. 2.
Figure 4:
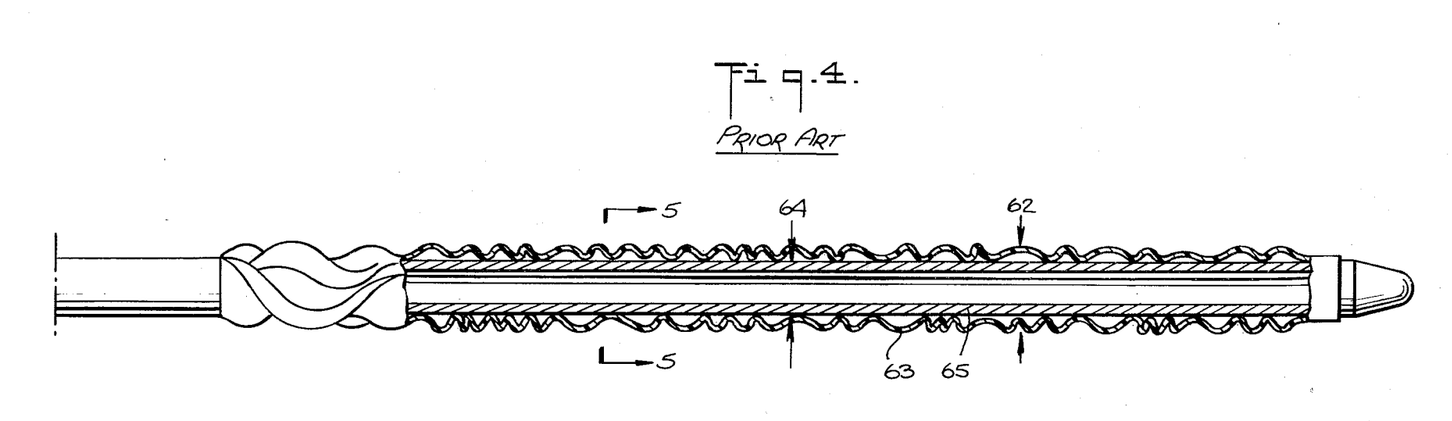
FIG. 4 is a side view, partly in section, of a prior art catheter showing the balloon thereof in a rolled or twisted configuration.
Figure 5:
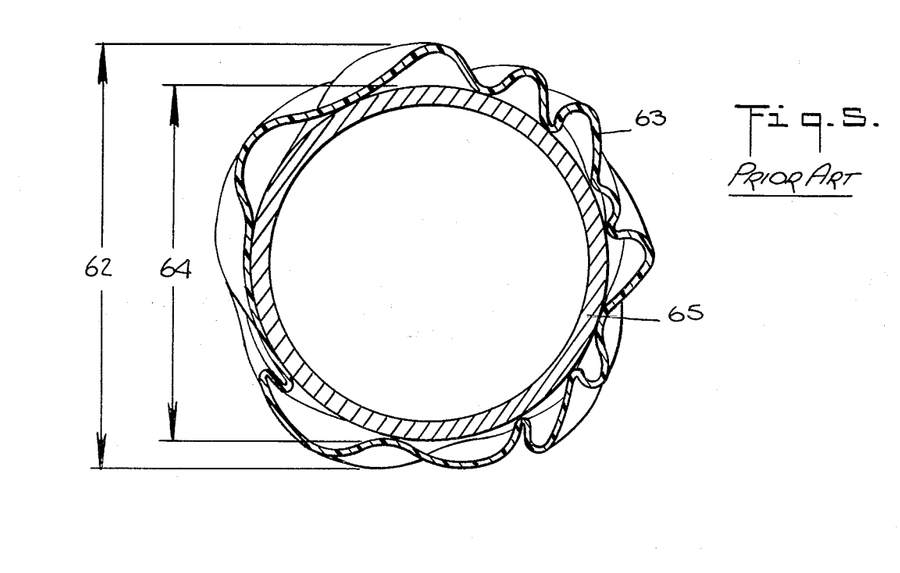
FIG. 5 is a section-view taken along line 5—5 of the prior art catheter of FIG. 4.

In use, balloon tip 32 is grasped and rotated to tightly twist balloon 28 about the thin wire support 50. Since the wire may be freely rotated within tube end 36, the tip may be rotated for many revolutions to impart a compact twist to the balloon as shown in FIG. 2. As the balloon is twisted about its own axis, its cross-sectional area is reduced, as shown in FIG. 3, and the cross-sectional area is inversely proportional to the number of rotations of the tip. Thus, the largest cross-sectional diameter of the catheter is that of the twisted balloon which approaches that of tip 32 and gas supply tube 22. A vacuum is applied to the interior of the wound balloon to keep it from unwinding. After insertion when the balloon is in the desired position, the vacuum is removed and the balloon unwinds. In contrast, the much larger cross-sectional configuration of a prior art catheter in which the ballon is wrapped on the interior support or catheter tube is shown in FIGS. 4 and 5. The largest cross-sectional diameter 62 of the wrapped balloon 63 is considerably larger than the cross-sectional diameter 64 of the catheter tube 65.

After the balloon has been twisted about the support wire as shown in FIGS. 2 and 3, a sheath 66 (FIG. 1) may be slid over the balloon to enclose it and enhance performance of the catheter. However, it is to be understood that the present invention as described above may be practiced without the sheath and that the sheath may be used to enhance performance. The sheath also prevents the balloon from unwinding. When a sheath is used, the vacuum may optionally be applied to the interior of the wound balloon. The sheath 66 is thin-walled and made of a low friction flexible material such as Teflon, Mylar or polyethylene. When used, it is positioned on the gas supply tube 22 adjacent the balloon 28 (FIG. 1) prior to its being drawn over the twisted balloon. In addition to locking the balloon in its twisted configuration, the sheath is smooth-walled and, as mentioned, is made of low friction material to facilitate insertion of the catheter. Sheath 66 is sufficiently long so that a portion thereof remains exposed after the catheter has been advanced to the desired location. The exposed portion is used to withdraw the sheath from over the twisted balloon and return it to its position on the gas supply tube 22. The balloon will then unwind due to the elastomeric nature of the balloon material and the inflating gas pressure. The sheath facilitates atraumatic entry of the catheter into the incision and blood vessel and facilitates insertion and guiding of the catheter in the blood vessel, however, as mentioned, use of the sheath is not mandatory.

A gas supply source 68 is connected to the catheter by means of the connector 26 and supplies and withdraws gas to the gas chamber 30 through gas supply tube 22 to achieve phasic operation of the catheter for the intra-aortic balloon pumping procedure.

The support wire 50 is preferably made of a material which may be formed during use into a desired axial configuration by bending. For example, the surgeon may bend the support wire near the distal tip 32 of the balloon to facilitate entry of the catheter into a tortuous blood vessel or bifurcation. The shape of the support wire may be formed with or without the balloon twisted thereabout.

Figure 6:
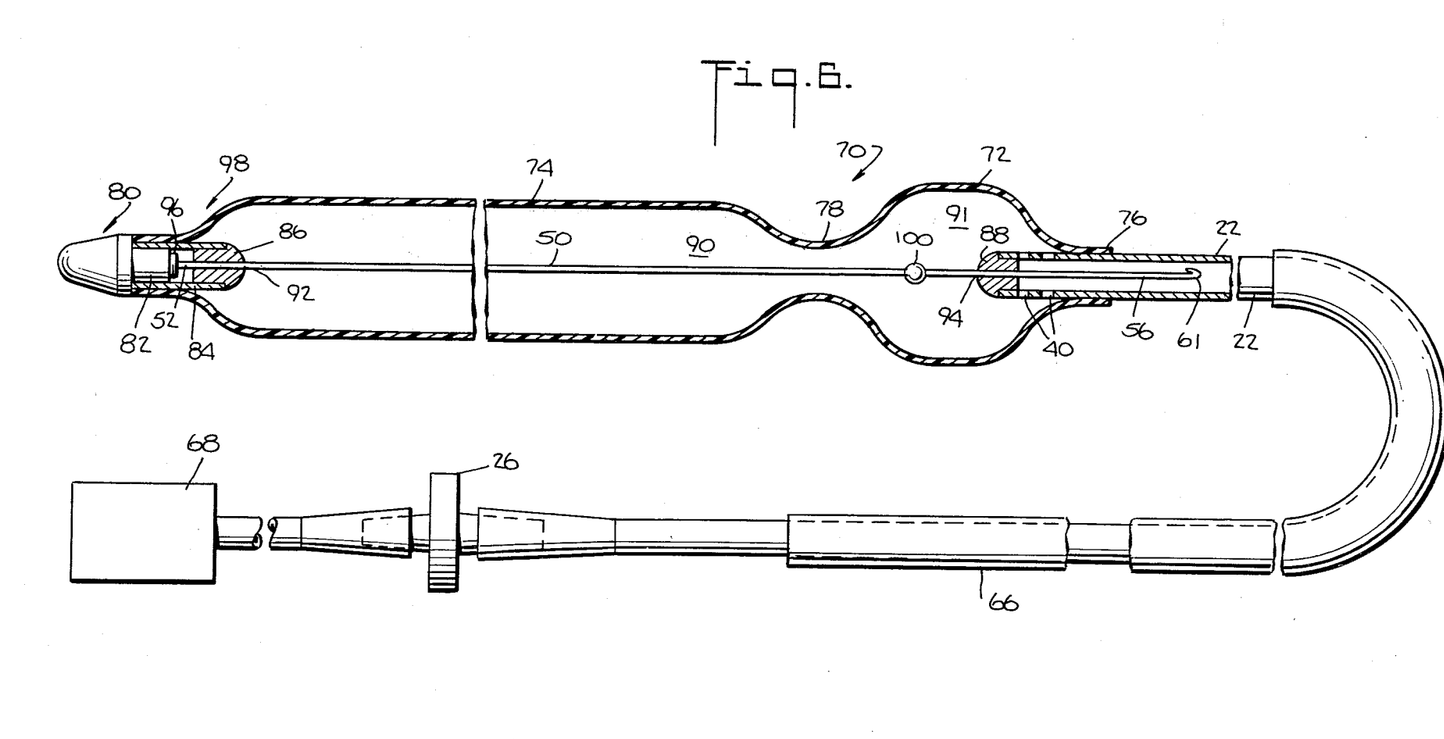
FIG. 6 is a side view, partly in section, of a dual-chamber catheter according to another embodiment of the invention.

The present invention may be embodied in dual or multi-chamber catheters in addition to the single chamber catheter described hereinbefore. Referring to FIG. 6, dual-chamber catheter 70 includes a second or occluding balloon section 72 in addition to the pumping balloon section 74 similar to balloon 28 of FIG. 1. Occluding balloon section 72 is bonded to tube 22 at end 76 of the balloon as described for balloon 28. The neck 78 between the balloon sections insures that the occluding balloon 72 is inflated before the pumping balloon 74 is inflated, thereby insuring optimal unidirectional balloon pumping action. It is understood, however, that the position of the occluding balloon 72 may be other than between balloon 74 and connector 26. In some instances, unidirectional pumping is more efficacious if the occluding balloon 72 is placed between tip 32 and the pumping balloon as shown in FIG. 3 of Grayzel, U.S. Pat. No. 3,939,820. While a single balloon is shown which forms separate balloon chambers, the multi-chambered catheter may comprise separate balloons. The distal tip and proximal end of the catheter tube may be configured as shown and described for the balloon catheter of FIG. 1. Alternatively, a rigid tip 80 may be provided having a section 82 of reduced diameter, a sleeve 84 and a plug 86. The sleeve is fluid-tightly circumferentially bonded about section 82 and the balloon end is fluid-tightly circumferentially bonded to the sleeve by, for example, an adhesive or by welding. The parts of tip 80 and tube 22 including plugs 86 and 88 within the chambers are smoothly contoured to reduce stress and wear on the balloon during operation thereby preventing puncturing, cutting or rupturing of the balloon.

Interposed between tip 80 and tube 22 in chamber 90,91 is the support wire 50. End 52 of the support wire is non-rotatably secured in hole 92 of plug 86 and end 56 is rotatably disposed in hole 94 of plug 86. A disc 96 is soldered to the end 52 of the wire which protrudes through plug 86, the disc abutting against section 82 of tip 80. This, together with the securing of the wire within hole 92 by means of, for example, an adhesive, prevents movement of wire 50 towards the distal end 98 of the balloon. Wire 50 includes a section 100 of enlarged diameter adjacent plug 88 which prevents movement of the wire toward the proximal end 76 of the balloon and prevents the wire from being forced further into the plug and tube 22 when pressure is applied to the balloon tip during insertion of the catheter. Hole 94 is sized to permit wire 50 to rotate freely therein. Section 100 is shown to be a spherically-shaped keeper, however, other shapes will also be suitable. The end 56 of the wire extends sufficiently into tube 22 to prevent the wire from being withdrawn through hole 94 of plug 88.

Wire end 56 at the extremity 61 thereof is rounded to prevent damage to the wall of tube 22, as described for the catheter shown in FIG. 1.

The catheters according to the invention are fabricated of biologically acceptable material. The tube 22 is formed, for example, of polyurethane. Tip 32 is formed, for example, from stainless steel or Lexan and the connector, from polyethylene or polypropylene. Balloon 28 (72,74) is made, for example, of a thin film of polyurethane. Other biologically acceptable materials may also be used. Gases such as air, carbon dioxide and helium or liquids are used to inflate the catheter when used for intra-aortic balloon pumping.

Figure 7:
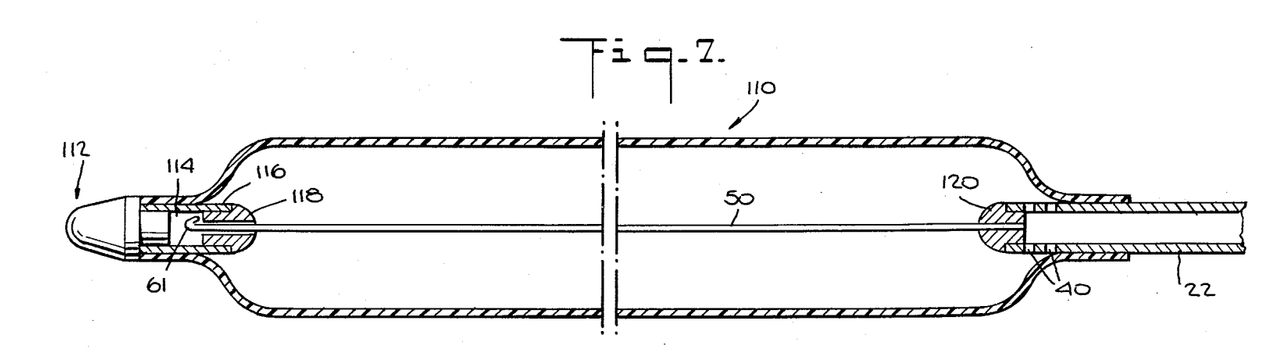
FIG. 7 is a sectional view of the balloon portion of a balloon catheter according to another embodiment of the invention in which the support means are rotatably coupled to the catheter tip.

While the invention has been illustrated with the support wire rotatably secured to the gas supply tube and non-rotatably connected to the distal tip, it is to be understood that it is contemplated according to the invention that the support wire may be rotatably secured to the distal tip and non-rotatably connected to the gas supply tube. Such an embodiment is illustrated in FIG. 7. Catheter 110 includes a tip 112 which has a hollow portion 114 therein. Tip 112 is similar to tip 80 illustrated in FIG. 6. In a manner similar to that described for tip 80 of FIG. 6, a sleeve 116 is bonded to tip 112 and a plug 118 is secured in sleeve 116. The support wire 50 extends through the central opening in the plug 118 and clearance is provided so that the wire is freely rotatable with respect to the plug. The support wire 50 terminates in a rounded section 61 in the hollow portion 114 of the tip 112. At the proximal end of the chamber, the support wire 50 is non-rotatably secured to the catheter tube portion 22 by means of, for example, a plug 120 similar to plug 88 illustrated in FIG. 6. The wire 50 terminates at plug 120 and is, for example, welded thereto.

In the embodiment illustrated in FIG. 7, the chamber is wound about the support means by grasping the distal end of the chamber and rotating the tip relative to the support wire and the proximal end of the chamber to wind the chamber about the support wire. In either case, the invention is practiced in that the balloon may be rotated relative to the support wire.

The advantages of the present invention, as well as certain changes and modifications of the disclosed embodiments thereof, will be readily apparent to those skilled in the art. It is the applicants' intention to cover by their claims all those changes and modifications which could be made to the embodiments of the invention herein chosen for the purpose of the disclosure without departing from the spirit and scope of the invention. Protection by Letters Patent of this invention in all its aspects as the same are set forth in the appended claims is sought to the broadest extent that the prior art allows.

What is claimed is:

1. A catheter comprising an inflatable and deflatable chamber having a proximal end and a distal end, said chamber in use being adapted to have substantially the same surface area when inflated and when deflated, a catheter tube portion connected at or adjacent an end thereof to the proximal end of said chamber and having a passage communicating with the interior of said chamber for admitting fluid into and withdrawing fluid from said chamber, support means for supporting said chamber extending in said chamber from the distal end thereof to said catheter tube portion and terminating in said catheter tube portion, said support means being non-rotatably connected to one of said ends of said chamber and rotatably coupled to the other of said ends of said chamber to permit relative angular motion between said support means and said chamber when said chamber is twisted about its longitudinal axis such that a configuration of said catheter may be obtained in which said chamber is wrapped about said support means, whereby insertion of said catheter into a body passageway or the like is aided.

2. The catheter recited in claim 1, wherein said support means is relatively rotatably coupled to the catheter tube portion at or adjacent the proximal end of said chamber and non-rotatably connected to said chamber at the distal end of said chamber.

3. The catheter recited in claim 2, wherein said chamber is non-rotatably connected to said catheter tube portion at the proximal end of said chamber.

4. The catheter recited in claim 1, wherein said support means is relatively rotatably coupled to the catheter tube portion at or adjacent the proximal end of said chamber.

5. The catheter recited in claim 4, wherein said chamber is connected at the proximal end thereof non-rotatably to said catheter tube portion.

6. The catheter recited in claim 5, wherein said catheter tube portion terminates in an opening which communicates the interior of said chamber and the interior of said catheter tube portion and wherein said support means comprises a rod-like member with one end thereof rotatably disposed in said opening and the other end thereof non-rotatably connected to the distal end of said chamber.

7. The catheter recited in claim 6 and further comprising a tip member disposed at the distal end of said chamber, said chamber terminating at said tip member and being connected fluid-tightly thereto, and wherein said rod-like member is non-rotatably connected to said tip member.

8. The catheter recited in claim 6, wherein said support means includes means for limiting axial movement of said rod-like member in said opening.

9. The catheter recited in claim 8, wherein said means comprises an enlarged section of said rod-like member disposed within said chamber adjacent said opening.

10. The catheter recited in claim 4 and including a plug terminating said catheter tube portion, said plug having an aperture which communicates the interior of said chamber and the interior of said catheter tube portion, and wherein said support means comprises a rod-like member with one end thereof rotatably disposed in said aperture of said plug and the other end thereof non-rotatably connected to the distal end of said chamber.

11. The catheter recited in claim 10 and further comprising a tip member disposed at the distal end of said chamber, said chamber terminating at said tip member and being connected fluid-tightly thereto, and wherein said rod-like member is non-rotatably connected to said tip member.

12. The catheter recited in claim 10, wherein said support means includes means for limiting axial movement of said rod-like member in said aperture of said plug member.

13. The catheter recited in claim 12, wherein said means comprises an enlarged section of said rod-like member disposed within said chamber adjacent said plug member.

14. The catheter recited in claim 1, wherein said support means is relatively rotatably coupled to the distal end of said chamber.

15. The catheter recited in claim 14, wherein said support means is non-rotatably connected to the proximal end of said chamber.

16. The catheter recited in claim 14, wherein said catheter includes a tip, said chamber distal end being non-rotatably connected to said tip and said support means being relatively rotatably coupled to said tip.

17. The catheter recited in claim 14, wherein said chamber proximal end and said support means are non-rotatably connected to said catheter tube portion.

18. A catheter comprising an inflatable and deflatable chamber having opposed ends, a catheter tube portion connected at or adjacent an end thereof to an end of said chamber, a rod-like member extending in said chamber between opposed ends thereof, said rod-like member having opposed ends one of which is disposed at or adjacent said end of said catheter tube portion and the other of which is disposed at the end of the chamber opposed from the end connected to the catheter tube portion, said rod-like member supporting said chamber and being non-rotatably connected to one of said ends of said chamber and rotatably coupled to the other of said ends of said chamber, said chamber being adapted to be rotated relative to said rod-like member to wrap said chamber about said rod-like member.

19. The catheter recited in claim 18, wherein the catheter tube portion includes a fluid passage therein in communication with the interior of said chamber and adapted to being communicated with a source of fluid, whereby the chamber may be inflated and deflated.

20. The catheter recited in claim 18, wherein said rod-like member is rotatably coupled to the distal end of said chamber and non-rotatably connected to the proximal end of said chamber.

21. The catheter recited in claim 18, wherein said rod-like member is non-rotatably connected to the distal end of said chamber and rotatably coupled to the proximal end of said chamber.

22. A catheter comprising an inflatable and deflatable chamber having opposed ends, said chamber having substantially the same surface area when inflated and when deflated, a catheter tube portion connected to one end of said chamber, a fluid passage in said catheter tube portion in communication with the interior of said chamber and adapted to be communicated with a source of fluid, whereby the chamber may be inflated and deflated, a rod-like member extending in said chamber between opposed ends thereof, said rod-like member having opposed ends, one of which is disposed at said catheter tube portion and the other of which is disposed at the end of the chamber opposed from the end connected to the catheter tube portion, said rod-like member supporting said chamber and being non-rotatably disposed with respect to one end of said chamber and rotatably disposed with respect to the other end of said chamber, one end of said chamber being adapted to be rotated relative to said rod-like member to wrap said chamber about said rod-like member.

23. The catheter recited in claim 22, wherein said rod-like member is rotatably coupled to the distal end of said chamber and non-rotatably connected to the proximal end of said chamber.

24. The catheter recited in claim 22, wherein said rod-like member is non-rotatably connected to the distal end of said chamber and rotatably coupled to the proximal end of said chamber.

25. The catheter recited in claims 19 or 22, wherein said catheter tube portion terminates in an opening which communicates the interior of said chamber and said fluid passage in said catheter tube portion and wherein one end of said rod-like member is rotatably disposed in said opening and the other end of said rod-like member is non-rotatably connected to the distal end of said chamber.

26. The catheter recited in claim 25 and further comprising a tip member disposed at the distal end of said chamber, said chamber terminating at said tip member and being connected fluid-tightly thereto, and wherein said rod-like member is non-rotatably connected to said tip member.

27. The catheter recited in claim 25, wherein said support means includes means for limiting axial movement of said rod-like member in said opening.

28. The catheter recited in claim 27, wherein said means comprises an enlarged section of said rodl-like member disposed within said chamber adjacent said opening.

29. The catheter recited in claims 19 or 22 and including a plug terminating said catheter tube portion, said plug having an aperture which communicates the interior of said chamber and said fluid passage in said catheter tube portion, and wherein said one end of said rod-like member is rotatably disposed in said aperture of said plug and the other end of said rod-like member is non-rotatably connected to the distal end of said chamber.

30. The catheter recited in claim 29 and further comprising a tip member disposed at the distal end of said chamber, said chamber terminating at said tip member and being connected fluid-tightly thereto, and wherein said rod-like member is non-rotatably connected to said tip member.

31. The catheter recited in claim 29, wherein said support means includes means for limiting axial movement of said rod-like member in said aperture of said plug member.

32. The catheter recited in claim 31, wherein said means comprises an enlarged section of said rod-like member disposed within said chamber adjacent said plug member.

33. The catheter recited in claims 1, 18, or 22 wherein said chamber includes two sections.

34. The catheter recited in claims 1, 18, or 25, and further comprising a thin-walled flexible sheath of low friction material adapted to enclose said chamber when the chamber is twisted on said support means.

35. The catheter recited in claim 34, wherein said sheath is open at opposed ends thereof and positioned on said catheter tube portion adjacent said chamber and is adapted to being drawn about said chamber to enclose it.

36. A balloon catheter having an inflatable and deflatable chamber which has substantially the same surface area when inflated and when deflated, said catheter including a catheter tube portion connected to said chamber at an end thereof and support means for supporting said chamber, said support means being non-rotatably connected to one of said ends of said chamber and rotatably coupled to the other of said ends of said chamber so that said chamber and said support means may be rotated relative to one another to facilitate wrapping of said chamber about said support means, a sheath for enclosing the wrapped chamber of said catheter to facilitate insertion thereof through an incision or a body opening, said sheath comprising an elongated, flexible, thin-walled member made of a material having a low coefficient of friction, the sheath being open at opposed ends thereof and being positioned about the catheter tube portion of the catheter adjacent the chamber and adapted to being drawn therefrom about the chamber to enclose it prior to insertion and further adapted to being withdrawn to said catheter tube portion after insertion.

* * * * *

REEXAMINATION CERTIFICATE (1357th)
United States Patent [19]

Hanson et al.

[11] B1 4,261,339

[45] Certificate Issued Sep. 25, 1990

[54] BALLOON CATHETER WITH ROTATABLE SUPPORT

[75] Inventors: Bruce L. Hanson, Wayne, N.J.; Sidney Wolvek, Brooklyn, N.Y.

[73] Assignee: Datascope Corp.

Reexamination Request:
No. 90/001,131, Dec. 1, 1986
No. 90/001,686, Jan. 6, 1989

Reexamination Certificate for:
Patent No.: 4,261,339
Issued: Apr. 14, 1981
Appl. No.: 883,513
Filed: Mar. 6, 1978

[51] Int. Cl.⁵ .......................................... A61M 25/10
[52] U.S. Cl. .................................................. 606/194
[58] Field of Search ....................................... 606/194

*Primary Examiner*—C. Fred Rosenbaum

*Attorney, Agent, or Firm*—Stevan J. Bosses

[57] ABSTRACT

An inflatable and deflatable balloon catheter is disclosed. The inflatable chamber of the catheter is supported about an elongated support member of small diameter. One end of the support member is rotatable relative to the chamber wherein the chamber is adapted to being compactly twisted about the support member upon swiveling or rotation of the support member. The compactly twisted chamber has a small diameter whereby insertion of the catheter through a small incision and guiding thereof in a small body canal or passage is facilitated. A smooth-walled sheath of low friction material is disclosed for enclosing the twisted chamber to facilitate atraumatic entry of the catheter into the incision or body opening and for facilitating insertion and movement of the catheter. The support member is preferably made of a material which may be formed during use into a desired axial configuration by bending. Balloon catheters according to the present invention are advantageously used for intra-aortic balloon pumping.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1-21 and 23-36 is confirmed.

Claim 22 is cancelled.

* * * * *